US011666205B2

(12) United States Patent
Duckett, III

(10) Patent No.: US 11,666,205 B2
(45) Date of Patent: Jun. 6, 2023

(54) METHOD FOR PRODUCING ENHANCED IMAGES WITH A SPLIT IMAGE ON COMMON IMAGE SENSOR

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 0 days.

(21) Appl. No.: 17/719,102

(22) Filed: Apr. 12, 2022

(65) Prior Publication Data

US 2022/0244462 A1 Aug. 4, 2022

Related U.S. Application Data

(62) Division of application No. 16/692,337, filed on Nov. 22, 2019, now Pat. No. 11,333,829.

(51) Int. Cl.
*A61B 1/00* (2006.01)
*A61B 1/05* (2006.01)
*A61B 1/06* (2006.01)
*G02B 6/27* (2006.01)

(52) U.S. Cl.
CPC ...... *A61B 1/00186* (2013.01); *A61B 1/00096* (2013.01); *A61B 1/00163* (2013.01); *A61B 1/00188* (2013.01); *A61B 1/05* (2013.01); *A61B 1/0676* (2013.01); *G02B 6/2706* (2013.01)

(58) Field of Classification Search
CPC . A61B 1/00163; A61B 1/00188; A61B 1/005; G06T 5/50; G06T 2207/20221
See application file for complete search history.

(56) References Cited

U.S. PATENT DOCUMENTS

| 8,339,479 | B2 | 12/2012 | Li |
| 8,606,009 | B2 | 12/2013 | Sun |
| 2002/0138008 | A1 | 9/2002 | Tsujita |
| 2008/0232131 | A1* | 9/2008 | Suda ................... A61B 1/0655 362/574 |
| 2012/0257077 | A1 | 10/2012 | Suzuki |
| 2012/0320164 | A1 | 12/2012 | Lipton |
| 2013/0038689 | A1 | 2/2013 | McDowall |
| 2013/0235174 | A1 | 9/2013 | Namii |

(Continued)

FOREIGN PATENT DOCUMENTS

WO 2019171642 A1 9/2019

OTHER PUBLICATIONS

Stöhr, J., M. G. Samant, "Liquid crystal alignment by rubedpolymer surfaces: a microscopic bond orientation model," J. Electron Spectroscopy, Elsevier, 1999, pp. 189-207, Amsterdam.

*Primary Examiner* — Aaron B Fairchild
(74) *Attorney, Agent, or Firm* — David Noel Villalpando

(57) ABSTRACT

Medical imaging camera head devices and methods are provided using light captured by an endoscope system or other medical scope or borescope. Afocal light from the scope is manipulated and split by a beamsplitter. At least one polarizing optical element manipulates the polarization properties of one or both of the beams. The resulting first and second beams are passed through focusing optics to different image sensor areas to produce images with different intensity. The resulting images are combined with high dynamic range techniques.

4 Claims, 8 Drawing Sheets

(56) References Cited

U.S. PATENT DOCUMENTS

| | | |
|---|---|---|
| 2014/0055661 A1 | 2/2014 | Imamura |
| 2014/0176692 A1 | 6/2014 | Tsuyuki |
| 2017/0238029 A1* | 8/2017 | Kiser ................ G06T 5/002 725/146 |
| 2019/0219831 A1 | 7/2019 | Duckett |

* cited by examiner

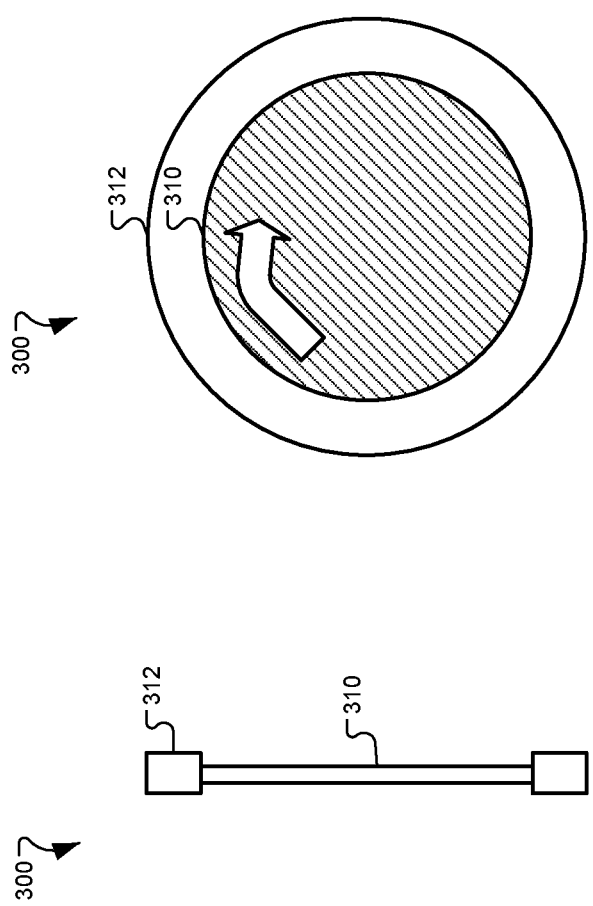

METHOD FOR PRODUCING ENHANCED IMAGES WITH A SPLIT IMAGE ON COMMON IMAGE SENSOR

CROSS-REFERENCE TO RELATED APPLICATIONS

This application is a division of U.S. patent application Ser. No. 16/692,337, filed Nov. 22, 2019, and entitled "Medical Imaging Device with Split Image on Common Image Sensor," issued as U.S. Pat. No. 11,333,829 B2 which is incorporated herein by reference.

TECHNICAL FIELD OF THE INVENTION

The invention relates generally to the field of medical image capture and more specifically to endoscopic camera designs with improved imaging.

BACKGROUND OF THE INVENTION

Dual image acquisition can be a useful feature in the field of endoscopy. Two video streams of the same scene are captured, but each of the captured image streams has different associated characteristics such as a variation in light spectrum, depth of field, or light intensity. In prior dual image systems, images have generally been collected, split in image space, and then focused onto two independent detectors. Such a configuration allows for more versatility than a single image acquisition system, but is generally more expensive and complex, requiring at least two sensors and associated electronics and mounting assemblies.

Some prior art systems do capture multiple images from a single chip, however they generally contain a beamsplitter in the image space of the camera. Such designs have significant limitations due to lack of flexibility in positioning desired optical elements such as filters, lenses, and other elements in the optical paths after the beam is split. Further, the cost of a dual image system may be higher due to the duplication of certain optical components used in focusing and detecting the image light of the dual channels.

What is needed are devices and methods to enable an endoscopic camera to acquire dual images in a cost effective manner. What is further needed are devices allowing the use of varied existing endoscopes for dual imaging applications, and allowing the detection of the varied characteristics in the dual images.

SUMMARY OF THE INVENTION

It is an object of the invention to provide improved endoscope acquisition of dual images, and to allow the use of varied existing endoscopes for dual imaging applications. It is another object to make the most effective use of high definition image sensors in dual imaging applications. It is a further object of the invention to allow detection of varied characteristics in the dual images, based on ability to vary the characteristics of the optical channels of the dual images.

Endoscopic camera head devices and methods are provided using light captured by an endoscope system. Substantially afocal light from the endoscope is manipulated and split by a beamsplitter. At least one polarizing optical element manipulates the polarization properties of one or both of the beams. The resulting first and second beams are passed through focusing optics to different image sensor areas to produce images with different intensity. The resulting images are combined with high dynamic range techniques.

According to a first aspect of the invention, an optical imaging system is provided for use with an endoscope. The optical imaging system includes a first optical group including a beamsplitter optically arranged to receive single optical image light in an afocal state and split the single optical image into a first portion of light directed along a first optical path and a second portion of light directed along a second optical path. A second optical group includes refractive elements optically arranged to receive the first and second portions of light from the beamsplitter and focus the first portion as a first image onto a first area of a first image sensor and focus the second portion as a second image onto either a second area of the first image sensor, wherein the first and second image areas of the first sensor do not overlap, or onto a second image sensor. A polarizing optical element is located upstream of the second optical group and operates to manipulate one or more of the single optical image light, the first portion of light and the second portion of light, the polarizing optical element capable of manipulating the polarization of the light entering it to produce an effect of controlling the relative intensity of the first image with respect to the second image.

According to some implementations of the first aspect, the polarizing optical element modifies the relative intensity of the first image with respect to the second image dynamically based on the content of the received image, such as a camera control unit (CCU) determining that a captured frame is underexposed, and adjusting settings as appropriate in the subsequent frame. The polarizing optical element may be a polarizer that rotates, thereby adjusting the relative intensity of the first and second images. The polarizing optical element may include a polarizer and a variable retarder, arranged such that when a retardance of the variable retarder is varied, the relative intensity of the first and second images with respect to each other is modified.

According to some implementations of the first aspect, the polarizing optical element is distal to the beamsplitter and controls the polarization of light entering the beamsplitter.

According to some implementations of the first aspect, the polarizing optical element is proximal to the beamsplitter. In some implementations, the polarizing optical element controls light from either the first or second optical path but not both.

According to some implementations of the first aspect, the beamsplitter reflects light that is highly polarized with respect to a designated polarization axis along the second optical path, while transmitting light that is partially polarized along the first optical path.

According to some implementations of the first aspect, the beamsplitter transmits light that is highly polarized with respect to a designated polarization axis along the first optical path, while reflecting light that is partially polarized along the second optical path.

According to some implementations of the first aspect, the first and second images are imaged onto a common sensor.

According to some implementations of the first aspect, the beamsplitter splits the single optical image light based on polarization, resulting, thereby, in the first and second portions of light from the beamsplitter having different polarization qualities.

According to a second aspect of the invention, a method is provided for producing enhanced images from a medical scope. The method includes collecting image light from an illuminated scene. The image light is directed light from the medical scope along a single optical channel with the image light in a substantially afocal state. The image light is split from the single optical channel into a first portion of light and a second portion of light.

The method includes adjusting an intensity of the first portion of light relative to the second portion of light by manipulating the polarization properties one or more of the image light directed along a single optical channel, the first portion of light, and the second portion of light. The first portion of light is directed along a first optical path and the second portion of light along a second optical path. The first portion of image light is focused on a first area of an image sensor and forming thereby a first detected image. The second portion of image light is focused on a second portion of the image sensor, separate from the first area of the image sensor, and forming thereby a second detected image.

According to some implementations of the second aspect, the method may include processing image data from the first and second portions of the image sensor to generate a single combined image with higher dynamic range than either the first or second detected image taken individually.

According to some implementations of the second aspect, adjusting an intensity of the first portion of light relative to the second portion of light may include rotating a polarizing element placed within the path of one or more of the image light, the first portion of light or the second portion of light.

According to some implementations of the second aspect, splitting the image light may include splitting the image light based on polarization, resulting, thereby in the first portion of light having different polarization properties from the second portion of light.

According to some implementations of the second aspect, the method includes modifying the relative intensity of the first image with respect to the second image dynamically based on the content of the received image, such as the CCU determining that a captured frame is underexposed, and adjusting settings as appropriate in the subsequent frame. Such modification may include rotating a polarizing optical element.

According to some implementations of the second aspect, modifying the relative intensity of the first image with respect to the second image includes varying the retardance of a variable retarder paired with a polarizer, such that when a retardance of the variable retarder is varied, the relative intensity of the first and second images with respect to each other is modified.

According to some implementations of the second aspect, the first and second images are imaged onto a common sensor.

BRIEF DESCRIPTION OF THE DRAWINGS

The present invention will become more fully understood from the detailed description given herein and the accompanying drawings which are given by way of illustration only, and thus are not limitative of the present invention, and wherein:

FIG. 3 shows a cross section diagram of a polarization control element constructed as a rotating polarizer according to some embodiments;

FIG. 4 is a front view diagram of the same polarization control element;

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video. Directions such as upstream and downstream refer to the direction of light travel.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
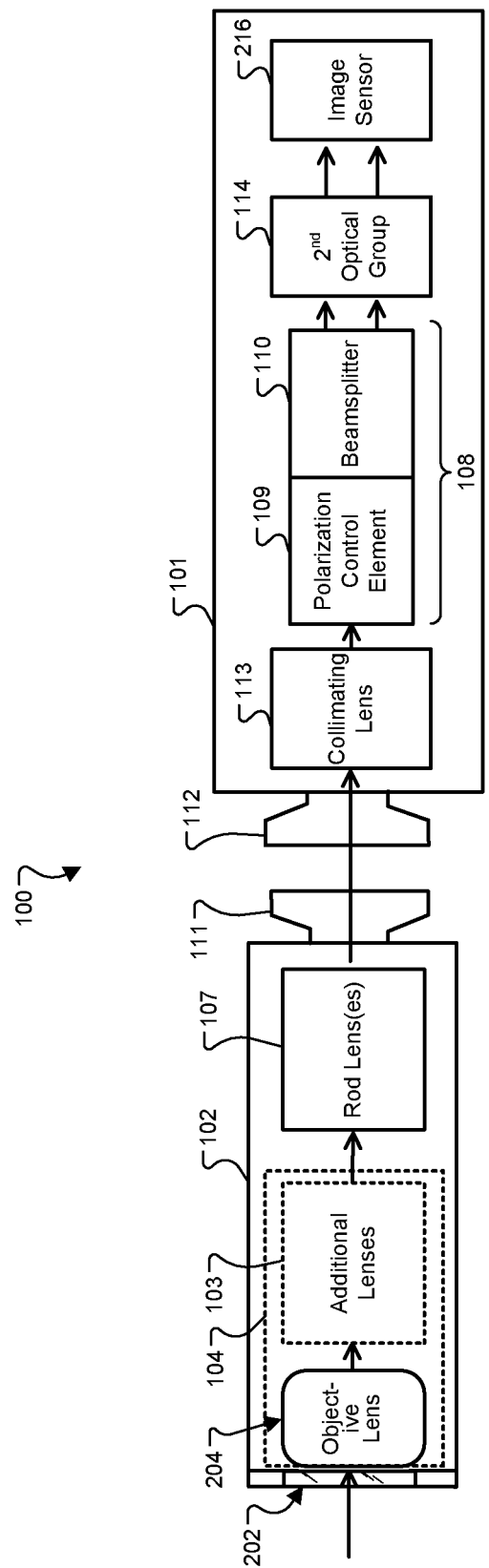
FIG. 1 is a block diagram of a medical imaging device 100 according to an example embodiment of the invention.

FIG. 1 is a block diagram of a medical imaging device 100 according to an example embodiment of the invention. Medical imaging device 100 ("device 100") includes a camera head 101 which may have an endoscope 102 attached via connectors 111 and 112. In some embodiments, an endoscope 102 and camera head 101 may be integrated into a single housing with no connectors needed. In some embodiments, the device 100 is provided as only the camera head 101 adapted to be connected to a suitable endoscope. Connectors 111 and 112 in this embodiment are standard eyecup style optical connectors but may be any suitable connector allowing light to pass from endoscope 102 to camera head 101. Various structural components supporting the depicted elements are omitted in the diagrams herein, as well as other components such as illumination lights sources and controls, which are known in the art and are not shown in order to avoid obscuring the relevant details of the example embodiments of the invention.

Camera head 101 includes a collimating lens 113 positioned at or behind a central window of connector 112 to receive and condition optical image light from the endoscope 102. Positioned in the optical channel after collimating lens 113 is a first substantially afocal optical group 108 that includes a polarization control element 109 optically arranged to receive the optical image light and alter the polarization properties of the image light, and a beamsplitter 110. By the term "substantially afocal," it is meant that the optical group 108 as a whole does not have a significant focusing effect on the imaging light passing there through, and, in addition, the optical group 108 is not positioned in the image space of the optical system, and does not receive focused image light.

Polarization control element 109 is preferably an adjustable control element which is able to vary the polarization properties of the image light over time. For example, polarization control element 109 may be a rotating polarizer which in operation is rotated to vary the relative intensity of the two portions of light produced by beamsplitter 110. Polarization control element 109 may also be constructed with a linear polarizer followed by a variable retarder. In such an embodiment, there is no physical rotation, and polarization is controlled by varying the retardance of the variable retarder. Examples of constructing polarization control element 109 will be further described below.

Beamsplitter 110 is optically arranged to receive the optical image light from polarization control element 109 and split the optical image light into a first portion of light directed to a first optical path and a second portion of light directed to a second optical path as depicted by the two arrows showing the light path to common second optical group 114. Beamsplitter 110 may be a polarization beamsplitter for passing light of different polarization properties in the first and second optical paths. The polarization beamsplitter acts in concert with polarization control element 109 to vary the relative intensity of the two portions of light in the first and second optical paths. The use of a common image sensor allows efficient use of high resolution sensors, which provide enough pixel resolution to capture a plurality of images with sufficient resolution for many endoscope applications.

The second optical group 114 is generally for focusing the substantially afocal light received from the first optical group 108 onto the image sensor. Second optical group 114 includes refractive elements optically arranged to receive the first and second portions of light from the beamsplitter 110 and focus the first portion as a first image onto a first area of a common image sensor 216 and the focus second portion as a second image onto a second area the common image sensor 216, different from the first area. The second optical group 114 typically includes at least one focusing lens, with the group having a total positive power. Many suitable lenses and combinations of lenses may be used for second optical group 114. The sensor signal, containing two images, is generally processed to treat the image data of the two images separately, providing images with different intensity ranges can be used to provide a high dynamic range (HDR) single combined image with higher dynamic range than either the first or second image taken individually. Such processing is described further below.

In some embodiments, system 100 includes an endoscope 102 as depicted at the left of the block diagram. The depicted endoscope is an example only, and many endoscope and borescope designs are suitable, including rigid and flexible endoscopes and borescopes. The exemplar endoscope 102 includes a cover glass 202 at its distal tip, which in this version faces directly along the longitudinal axis of the endoscope 102, but may also be positioned at an angle relative to the longitudinal axis as is known in the art. Behind, or on the proximal side of, the cover glass 202 is shown a preferred position for the objective lens 204, set against or very near cover glass 202 and preferably assembled together with the cover glass in construction. While a wide-angle lens is preferred for objective lens 204, this is not limiting and any suitable lens may be used in various embodiments. Objective lens 204 may be part of an objective lens group 104 which may include one or more additional lenses 103. The particular number and arrangement of lenses in the endoscope 102 will vary widely depending on the application. Optically arranged or attached at the proximal side of objective lens 204 or objective lens group 104 is a series of one or more rod lenses 107 that serve to pass the light down endoscope 102 towards its proximal end. Typically several rod lenses 107 are employed, which may be separated by spacers or other lenses in any suitable manner known in the art. Also, while the endoscope 102 is typically rigid, known shaft design variations allow rod lenses to be used in a semi-flexible shaft in which flexible joints are present at one or more places along the shaft between the rod lenses while the shaft is rigid along the portions containing a rod lens. Such a shaft design may be used in various embodiments of the invention.

Figure 2:
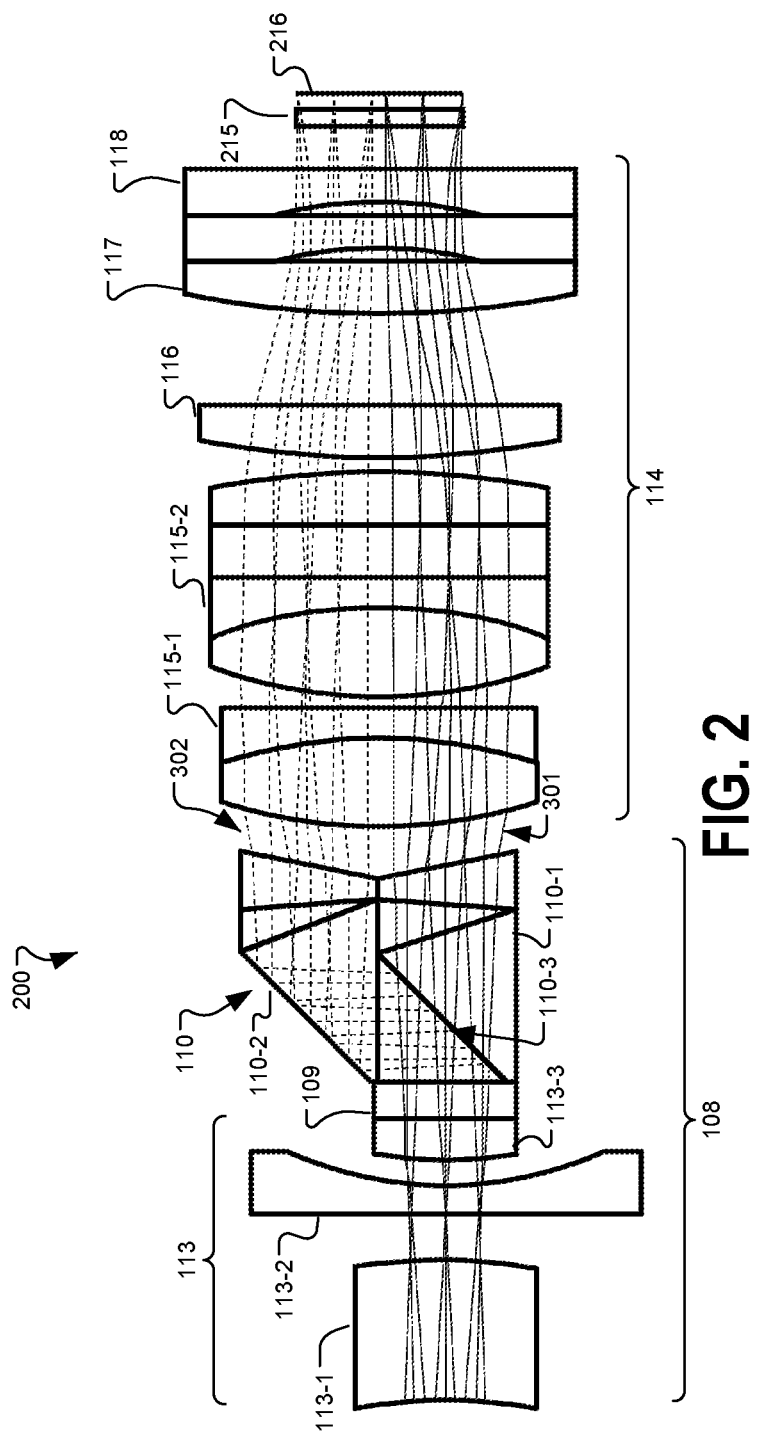
FIG. 2 is a cross section diagram of an optical assembly of a camera head according to some embodiments.

FIG. 2 is a cross section diagram of an optical assembly of camera head 101 of FIG. 1. The view includes a light ray diagram showing the passage of image light through the optical assembly to image sensor 216. The depicted optical elements are in diagram form only and are not drawn to scale. Optical assembly 200 including a first optical group 108 starts at collimating lens group 113 which receives light entering camera head 101 from an attached endoscope. The image light is received from the scope and directed along a single optical channel of first optical group 108 to collimating lens group 113. Collimating lens group 113 may have a slightly positive or negative power in order to adjust the image light to the desired condition to be received by beamsplitter 110. Collimating lens group 113 includes lenses 113-1, 113-2, and 113-3. Concave-convex lens 113-1 optically arranged to receive the image light and having a negative optical power, spreading the image light to a desired size and mitigating ghost reflections. Optically arranged in the proximal direction from lens 113-1 is plano-concave lens 113-2, which has a negative optical power to align the image light. Optically arranged along the concave area of lens 113-2 is convex-plano lens 113-3, with a positive power for further conditioning the light for passage to beamsplitter 110.

A polarization control element 109 is optically positioned between collimating lens group 113 and beamsplitter 110. Polarization control element 109 is arranged to receive the optical image light from collimating lens group 113 and alter the polarization properties of the image light. As discussed above, polarization control element 109 is preferably adjustable and may be constructed in a number of suitable ways, such as shown in the examples of FIG. 3 and FIG. 4.

Beamsplitter 110 is optically arranged to receive the optical image light in an afocal state from an endoscope, via the collimating lens group 113 and polarization control element 109, and split it into a first portion of light directed to a first optical path 301 passing through prism group 110-1 and a second portion of light directed to a second optical path 302 passing through prism group 110-2. Beamsplitter 110 is constructed of prisms, including a right-angle prism and triangular prism with a joint having suitable partially reflective coating along their adjacent surface at interface 110-3, by which the image light is split with a first portion passing straight through along first optical path 301 and a second portion reflected upward along second optical path 302 as depicted.

As discussed above, the first and second portions of light may comprise light with different polarization conditions, with the reflective coating at interface 110-3 being sensitive to polarization to produce a polarization beamsplitter. This is typically accomplished by reflecting or passing light with designated polarization conductions at interface 110-3. For example, interface 110-3 may reflect light that is highly polarized with respect to a designated polarization axis along the second optical path, while transmitting light that is partially polarized along the first optical path. Or, interface 110-3 may transmit light that is highly polarized with respect to a designated polarization axis along the first optical path, while reflecting light that is partially polarized along the second optical path. The designated axis or condition may be selected using the traditional S and P polarization axes, or may include passing or reflecting circularly polarized light. Polarization control element varies the polarization properties of the incoming light over time, such that the relative intensity of the first and second portion of light is varied as the light is passed and reflects in differing ratios at interface 110-3. These two portions of light with differing intensity are then detected at image sensor 216 and employed to produce an HDR image.

Beamsplitter 110 is constructed in this embodiment with multiple angled prisms in order to produce a symmetrical arrangement of optical paths 301 and 302, with each path including a triangular prism and a wedge-shaped prism, resulting in the longitudinal axes of both assemblies along optical paths 301 and 303 to be parallel to that of light received by the beamsplitter 110. Other versions may employ other suitable prism arrangements allowing an optical axis of the camera head 101 optics to be non-parallel to the camera head 100 optical assembly.

The second optical group 114 includes refractive elements optically arranged in both the first and second optical paths 301 and 302 to receive the first and second portions of light from the beamsplitter 110 and focus the first portion as a first image onto a first area of a common image sensor 216 and the focus second portion as a second image onto a second area the common image sensor 216, different from the first area. Both optical paths 301 and 302 are incident on a doublet achromat lens 115-1, which has a positive optical power, including a biconvex lens and a concave-plano lens. The camera head 100 optical group is positioned with the axis pointing between the first and second paths such that each path has similar incidence on lens 115-1. Optically arranged in the proximal direction to doublet achromat lens 115-1 is a second lens group 115-2 including a doublet lens, a flat plate, and a plano-convex lens, and having a total positive optical power as indicated by the converging effect on the depicted ray lines.

While lens assemblies 115-1 and 115-2 are shown, other suitable optical assemblies may be used. For example, the optical assembly may use a Petzval lens or lens group with a field flattener, or other suitable lens or lens group presented at the camera head 200 aperture that is capable of a very large aperture and has a field flattening effect with positive powered elements in front and a negative powered field flattener near the image plane. This is convenient in this system because the two optical paths will be separated at the front lens and the aperture must be large enough to accommodate both. Optically arranged next is a convex-plano lens 116 which further focuses both portions of light toward the sensor.

Optically arranged to receive both portions of light from lens 116 is a lens 117, having a positive power. Optically arranged next are two smaller plano-concave lenses 118 with a negative power, directing both portions of light toward cover glass 215 and image sensor 216. Lenses 118 direct both portions of light to create a pair of images of the desired size at image sensor 216. Finally, the process includes processing the first and second image to generate a single combined image including first characteristics having a first dynamic range from the first portion of light and second characteristics having a second dynamic range, different from the first, from the second portion of light. This may be implemented, for example, with image processing hardware as described with respect to FIG. 9. Processing the image data with different intensity ranges is used to provide a high dynamic range (HDR) single combined image with higher dynamic range than either the first or second image taken individually. With the two images taken with different polarization characteristics in the image light, further advantages may be achieved such as glare reduction and improved feature visibility over a traditional HDR imaging technique.

FIG. 3 shows a cross section diagram of a polarization control element 300 constructed as a rotating polarizer according to some embodiments. FIG. 4 is a front view diagram of the same polarization control element 300. Polarization control element 300 includes a housing 312 forming a circular opening in which a polarizing filter 310 is rotatably mounted. Rotating movement of polarizing filter 310 is depicted by the arrow. Construction of rotating polarizers is known in the art, and may include an electric motor or other drive mechanism mounted in housing 312 and operable to produce the rotation using a drive gear matched to grooves along the perimeter of polarizing filter 310. In operation, the drive mechanism may rotate polarizing filter 310 as needed, in variable or discrete movements upon command.

Figure 5:
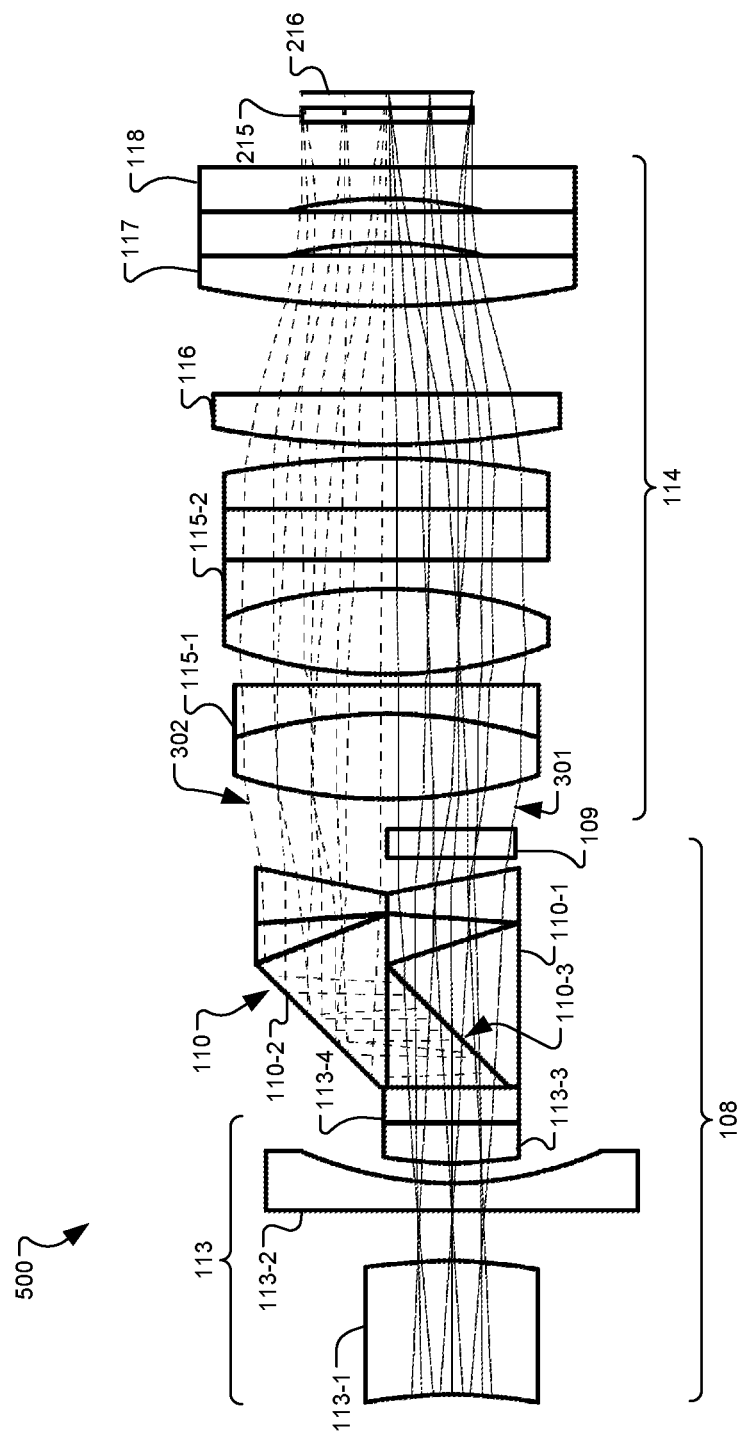
FIG. 5 is a cross section diagram of another optical assembly of camera head of FIG. 1 according to some embodiments.

FIG. 5 is a cross section diagram of another optical assembly of camera head 101 of FIG. 1 according to some embodiments. The cross section includes a light ray diagram showing the passage of image light through the assembly to image sensor 216. The depicted optical assembly 500 is largely similar to that of FIG. 2 and has similarly numbered elements. Collimating lens group 113 includes a flat plate 113-4 optically positioned between convex-plano lenses 113-3 and beamsplitter 110.

Rather than placing polarization control element 109 between collimating lens group 113 and beamsplitter 110, polarization control element 109 in this version is optically positioned in first optical path 301 following the beamsplitter 110. Polarization control element 109 does not extend into second optical path 302.

As with the other embodiments herein, the two images detected at sensor 216 are typically processed by the system camera control unit (CCU) to produce a final image based on both images.

Figure 8:
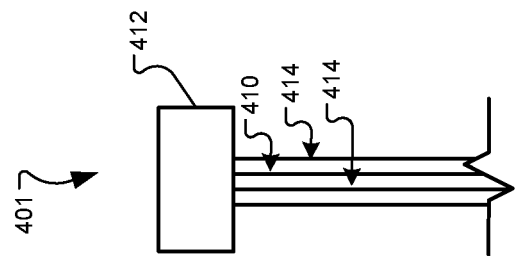
FIG. 8 shows an enlarged cross section view of the variable retarder of FIG. 6.
Figure 7:
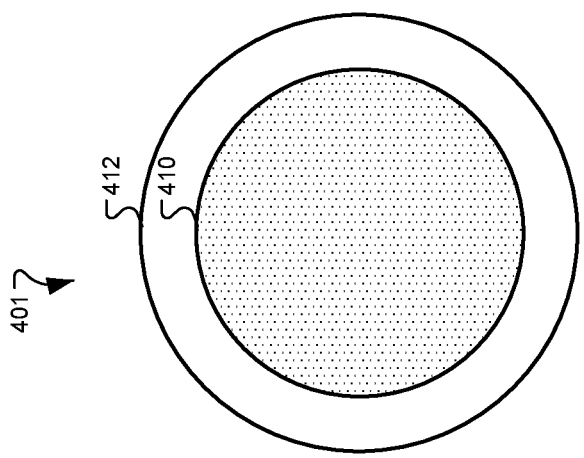
FIG. 7 shows a front view diagram of the variable retarder of FIG. 6.
Figure 6:
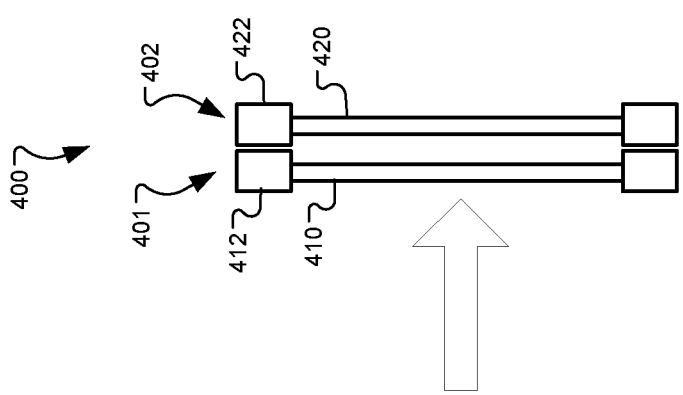
FIG. 6 shows a cross section diagram of a polarization control element including a variable retarder and a linear polarizer according to some embodiments.

FIG. 6 shows a cross section diagram of a polarization control element 400 including a variable retarder 401 and a linear polarizer 402 according to some embodiments. FIG. 7 shows a front view diagram of the variable retarder 401 of FIG. 6. FIG. 8 shows an enlarged cross section view of the variable retarder 401 of FIG. 6. Referring to FIGS. 6-8, polarization control element 400 may be used in the embodiment of FIG. 5 or other embodiments in which a polarization control element is optically arranged following a beamsplitter. Some embodiments employ polarization control element 400 upstream of the beamsplitter 110, however in these embodiments the polarization control element contains the polarizer 402 upstream from the variable retarder 401. Polarization control element 400 is depicted with an arrow in FIG. 6 showing the direction of light passage, first through variable retarder 401 and then through linear polarizer 402.

Variable retarder 401 includes a frame 412 with control electronics, and a retarding medium 410. In the cross-section of FIG. 8, the construction of one example retarding medium 410 is shown. Many suitable variable retarder technologies may be used, with a preference for those that can be miniaturized. In this embodiment, retarding medium 410 is a thin layer of a liquid crystal fluid sandwiched between two transparent electrodes 414. The liquid crystal molecules are highly anisotropic. When a voltage is applied to electrodes 414 through electrical circuitry in housing 412, an electric field between electrodes 414 orients the liquid crystal molecules. The field-induced orientation of the liquid crystal molecules causes a change in the index of refraction of the liquid crystal layer. This change results in alteration of the optical phase of light passing through the liquid crystal layer. In operation, variable retarder 401 is controlled to produce at least two different polarization conditions.

Linear polarizer 402 includes a frame 422 and a linear polarizing filter 420. Many different linear polarizer technologies may be used for linear polarizer 402. The orientation of the polarizing effect of linear polarizing filter 420 is selected to pass differing amounts of light for the different polarization conditions created by variable retarder 401.

Figure 9:
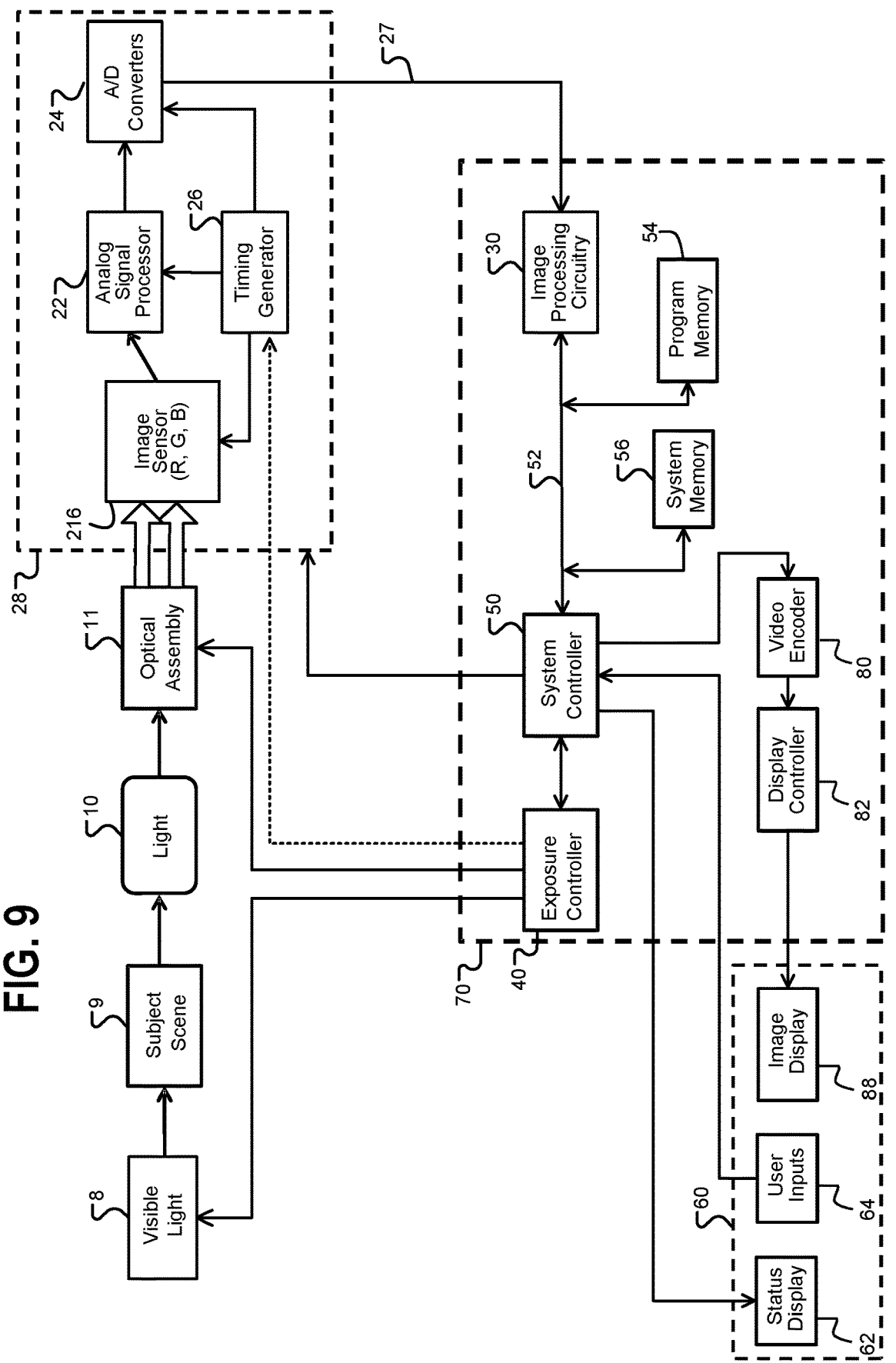
FIG. 9 shows a block diagram of system including an endoscope device and an image capture device having an improved dual image optical path as described above.

FIG. 9 shows a block diagram of system including an endoscope device and an image capture device having an improved dual image optical path as described above. The invention is applicable to more than one type of device enabled for image capture, such as FI-capable endoscopes, and other medical imaging devices. The preferred version is an imaging scope system, such as an endoscope.

The diagram shows a light source 8 which illuminates subject scene 9 with visible light. Fluorescent excitation light may also be used, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is split and modified as described herein, then passed to image sensor assembly 28 where it is focused to form two images at a solid-state image sensor 216. Optical assembly 11 includes the optics of the endoscope and of the camera head. As discussed above, portions of the optical assembly may be embodied in a camera head attached to a scope, or in a single imaging device. Image sensor 216 converts the incident light to an electrical signal by integrating charge for each picture element (pixel). The image sensor 216 may be constructed with any suitable sensor technology such as active pixel complementary metal oxide semiconductor sensor (CMOS APS) or a charge-coupled device (CCD), for example.

The total amount of light 10 reaching the image sensor 216 is regulated by the light source 8 intensity, the optical assembly 11 aperture, the attenuation in each optical path, and the time for which the image sensor 216 integrates charge. An exposure controller 40 responds to the amount of light available in the scene given the intensity and spatial distribution of digitized signals corresponding to the intensity and spatial distribution of the light focused on image sensor 216. If fluorescence imaging is used, exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 216 integrate charge. The control connection from exposure controller 40 to timing generator 26 is shown as a dotted line because the control is typically indirect.

Timing generator 26 produces various clocking signals to select rows and pixels and synchronizes the operation of image sensor 216, analog signal processor 22, and A/D converter 24. Image sensor assembly 28 includes the image sensor 216, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

Analog signals from the image sensor 216 are processed by analog signal processor 22 and applied to analog-to-digital (A/D) converter 24 for digitizing the analog sensor signals. The digitized signals each representing streams of images or image representations based on the data, are fed to image processor 30 as image signal 27. Typically both images will be transmitted together in signal 27 as a single image, which is separated in the image processing circuitry into dual image areas of the sensor (for example, image 1 and image 2, of FIG. 10).

The system camera control unit (CCU) 70 includes image processing circuitry 30 performing digital image processing functions to process and filter the received images as is known in the art. Image processing circuitry may include separate, parallel pipelines for processing the first and second images separately. CCU 70 may be implemented in a single assembly or may include two or more camera control modules performing different functions such as communication with a specific camera model and image processing. Such circuitry is known in the art and will not be further described here. Image processing circuitry 30 may provide algorithms, known in the art, for combining two images of the same view but containing different characteristics in a combined image display.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity and control timing that may be necessary to obtain image streams. Exposure controller 40 may also control and adjust the polarization control element in optical assembly 11. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between an individual view of either single image (for example, image 1 or image 2), both individual images, and/or a view of the combined image created with processing of data from both images. Settings may be provided to adjust the manner in which characteristics from the individual images are combined and displayed or stored. Settings may also include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80, and display controller 82 may be housed within CCU 70.

CCU 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 11:
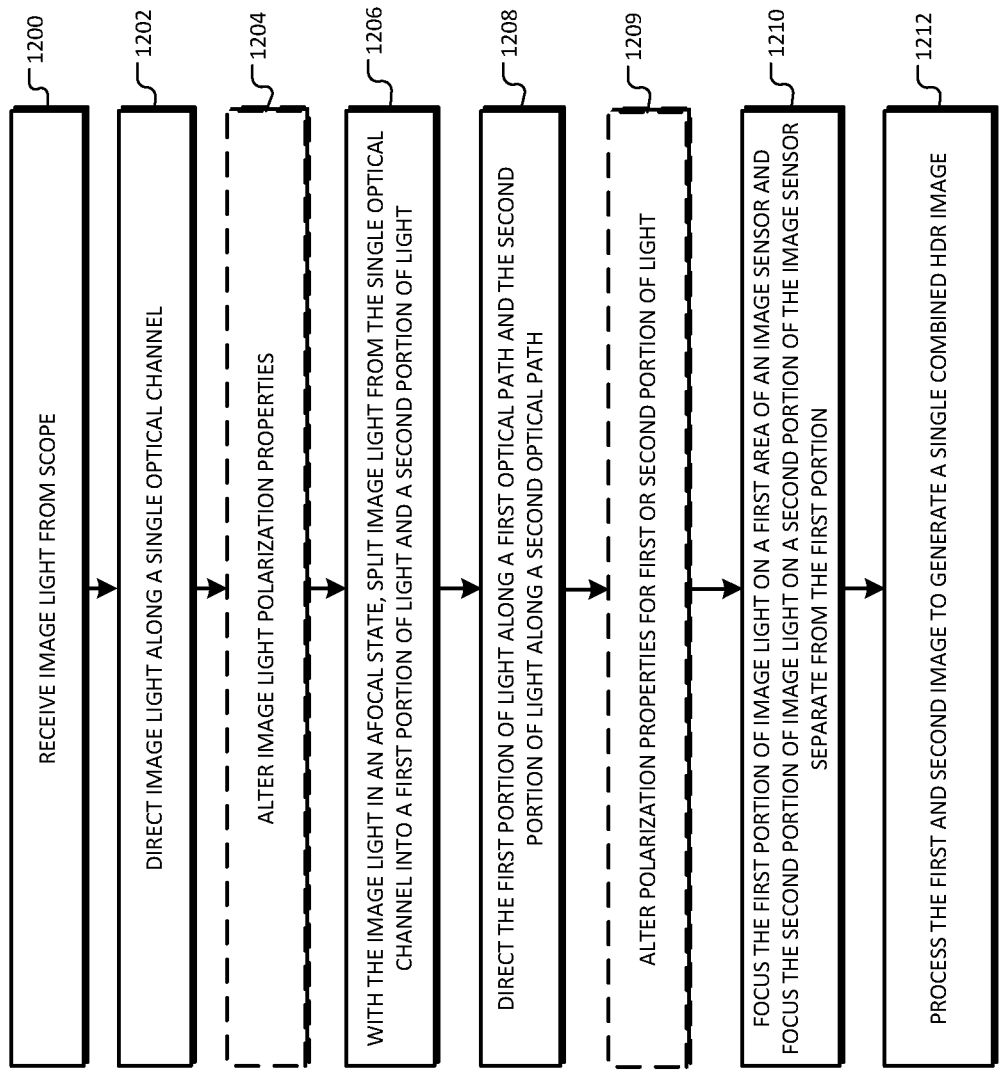
FIG. 11 is a flowchart of a process for producing high dynamic range images according to some embodiments.

FIG. 11 is a flowchart of a method for producing endoscopy images according to an example embodiment. The method may be performed employing any of the various example embodiments of a camera head or joint endoscope and camera head devices as described herein, with a suitable camera control unit such as that described above to process the image data. Other types of medical scopes or borescopes may be used in place of the endoscope as discussed above. The method begins at process block 1200 where it includes receiving the image light from an endoscope. The endoscope device used may be a separate device attached to a camera head or an endoscope integrated with a camera head. At process block 1202, the process directs the received image light along a single optical channel. At block 1204, the process may alter the polarization properties of the image light, still in a single optical channel. This may be done in a time varying manner, such as by rotating a rotating polarizer or varying a variable retarder. Some embodiments may not include block 1204.

Next at process block 1206, with the image light in an afocal state, the process includes splitting the image light from the single optical channel into a first portion of light and a second portion of light. Process block 1206 may also operate to manipulate the first and second resulting beams relative to each other by selecting of the characteristics of the resulting beams that are allowed to pass directly through or be reflected by the beam splitting means. For example, beam splitting means at block 1206 may include a polarizing beam splitter, resulting in the first portion of light having different polarization properties than the second portion of light. Then at block 1208, the process directs the first portion of light along a first optical path and the second portion of light along a second optical path. Directing the light is preferably done with a beam splitter such as the example beam splitters described herein. Optionally, at block 1209, the process may further optically manipulate the polarization properties of the first or second portion of light, such as by applying a variable retarder or polarization filter. One of blocks 1206 or 1209 manipulates the intensity of image light in one of the paths relative to the other path. This may be done by a polarizing beamsplitter which produces two beams having differing intensity based on the quantity of light which has the particular polarization properties separated by the beamsplitter. Or, the intensity of image light in one of the paths may be attenuated with a polarization filter or variable retarder and polarization filter arrangement such as that in FIGS. 5-8.

Figure 10:
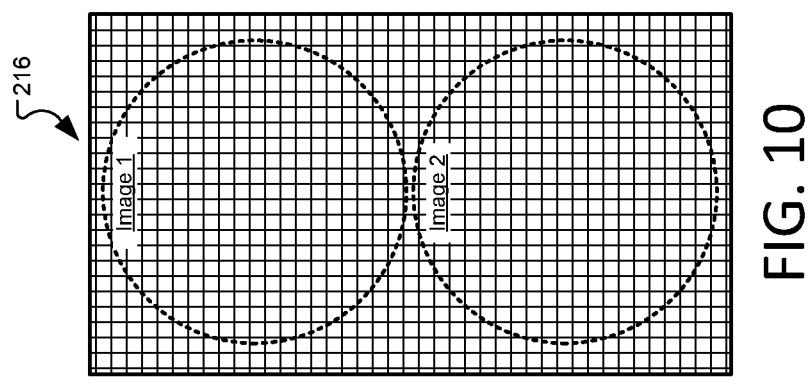
FIG. 10 shows a diagram of an image sensor area with multiple images according to some embodiments.

Next at process block 1210 the process includes focusing the first portion of image light on a first area of an image sensor and focusing the second portion of image light on a second portion of the image sensor separate from the first portion. An example of the resulting areas is depicted in FIG. 10, which shows example areas of rectangular image sensors 216, with the first portion of light hitting the sensor on the area shown as Image 1 and second portion of light hitting the sensor on the area shown as Image 2.

Next at process block 1212, image processing is performed on the image data from the sensor. The processing is generally applied to image data from both the first and second portions to generate a single combined image including first characteristics resulting only from the first portion of light and second characteristics resulting only from the second portion of light. The processing is performed by a CCU such as the CCU 70 of FIG. 9, or other suitable image processing circuitry. Processing the image data with different intensity ranges provides a high dynamic range (HDR) single combined image with higher dynamic range than either the first or second image taken individually. Known image processing techniques for polarization studies may be applied in processing the dual images from such an embodiment, permitting, for example, glare reduction in the combined image.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A method of producing enhanced images from a medical scope, comprising:
   collecting image light from an illuminated scene;
   directing collected image light from the medical scope along a single optical channel with the collected image light in a substantially afocal state,
   splitting the collected image light from the single optical channel, still in a substantially afocal state, into a first portion of light and a second portion of light;
   adjusting an intensity of the first portion of light relative to the second portion of light by manipulating the polarization properties one or more of the collected image light directed along a single optical channel, the first portion of light, and the second portion of light;
   directing the first portion of light along a first optical path and the second portion of light along a second optical path;
   focusing the first portion of image light, subsequent to splitting the collected image light, on a first area of a first image sensor and forming thereby a first detected image; and modifying the relative intensities of the first portion of image light with respect to the second portion of image light dynamically based on the content of the first and second detected images, this step of modification including varying the retardance of a variable retarder paired with a polarizer, such that when a retardance of the variable retarder is varied, the relative intensity of the first and second portions of image light with respect to each other is modified;
   focusing the second portion of image light, subsequent to splitting the collected image light, on either a second area of the first image sensor separate from the first area of the first image sensor, or on a second image sensor, and forming thereby a second detected image.

2. The method according to claim 1, further comprising processing image data from the first detected image and the second image to generate a single combined image with higher dynamic range than either the first or second detected image taken individually.

3. The method according to claim 1 wherein the splitting the image light comprises splitting the image light based on polarization, resulting, thereby in the first portion of light having different polarization properties from the second portion of light.

4. The method according to claim 1 wherein the first and second images are imaged onto a common sensor.

* * * * *